(12) United States Patent
Egan et al.

(10) Patent No.: US 6,217,591 B1
(45) Date of Patent: *Apr. 17, 2001

(54) SUTURE FASTENING DEVICE

(75) Inventors: Thomas D. Egan, Marblehead; Richard B. Streeter, Andover, both of MA (US)

(73) Assignee: Axya Medical, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/198,475

(22) Filed: Nov. 24, 1998

Related U.S. Application Data

(63) Continuation-in-part of application No. 08/919,297, filed on Aug. 28, 1997, now Pat. No. 5,893,880.
(60) Provisional application No. 60/066,879, filed on Nov. 24, 1997.

(51) Int. Cl.$^7$ ..................................................... A61B 17/04
(52) U.S. Cl. ........................................... 606/144; 606/145
(58) Field of Search ........................... 606/144, 145–147, 606/103, 228, 169, 27–30, 42, 45

(56) References Cited

U.S. PATENT DOCUMENTS

| | | | | |
|---|---|---|---|---|
| 3,513,848 | * | 5/1970 | Winston et al. | 128/335 |
| 4,662,068 | | 5/1987 | Polonsky | 30/124 |
| 5,383,883 | | 1/1995 | Wilk et al. | 606/169 |
| 5,417,700 | * | 5/1995 | Egan et al. | 606/144 |
| 5,893,880 | * | 4/1999 | Egan et al. | 606/228 |

* cited by examiner

*Primary Examiner*—Michael Buiz
*Assistant Examiner*—Lien Ngo
(74) *Attorney, Agent, or Firm*—McDermott Will & Emery

(57) ABSTRACT

A suture fastening device for forming a welded suture joint in situ includes a horn 8 and an anvil 16 movable relative to each other in a tubular shaft 3, and a source of energy 6 for actuating the horn and anvil within the shaft and relative to each other. Segments 20a, 20b of a suture to be joined are captured within the anvil and contacted by the horn for transfer of energy thereto during welding. A predetermined condition of the welded joint or of the horn and anvil is detected so as to control the delivery of energy to the segments during welding.

16 Claims, 8 Drawing Sheets

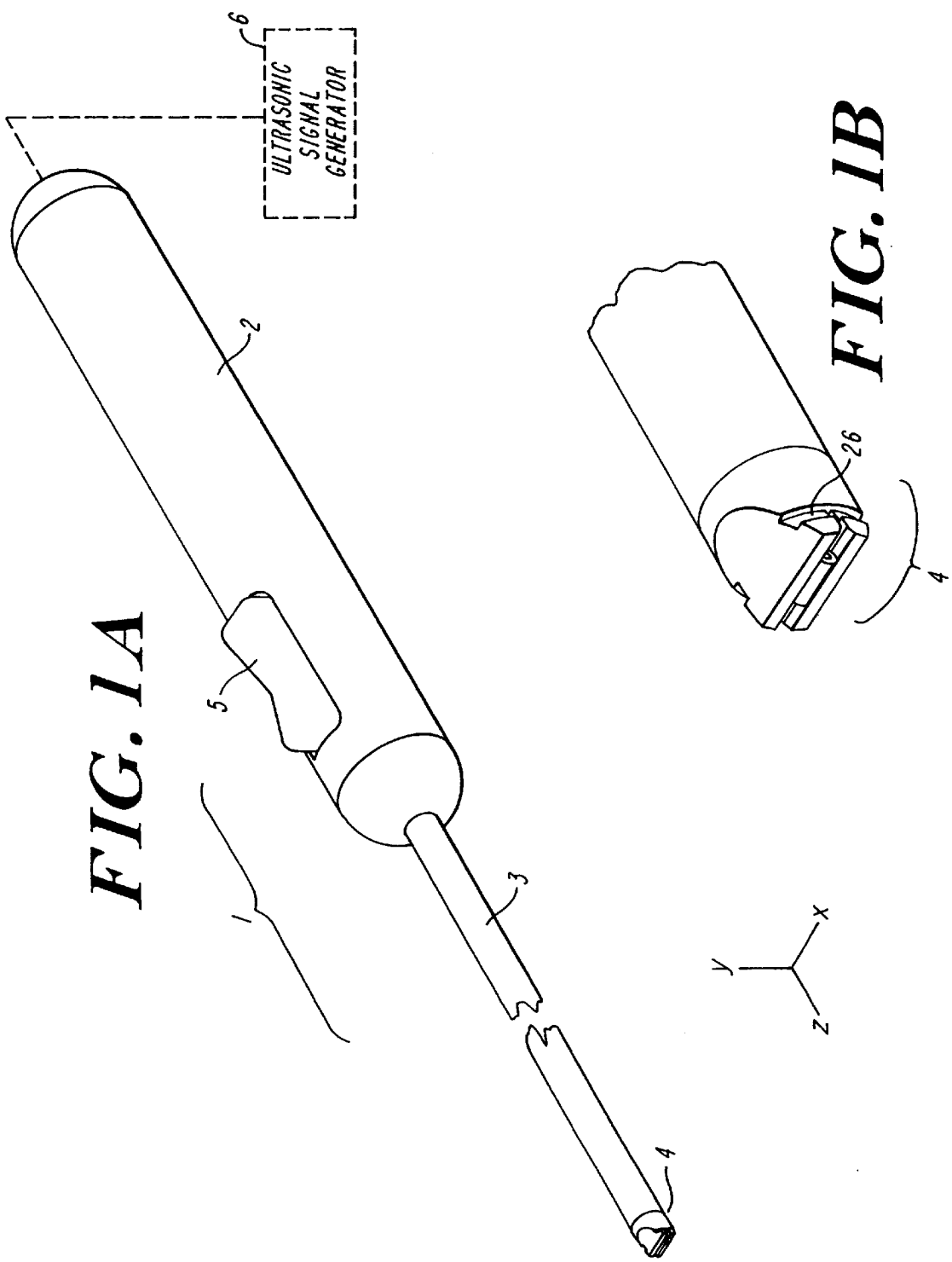

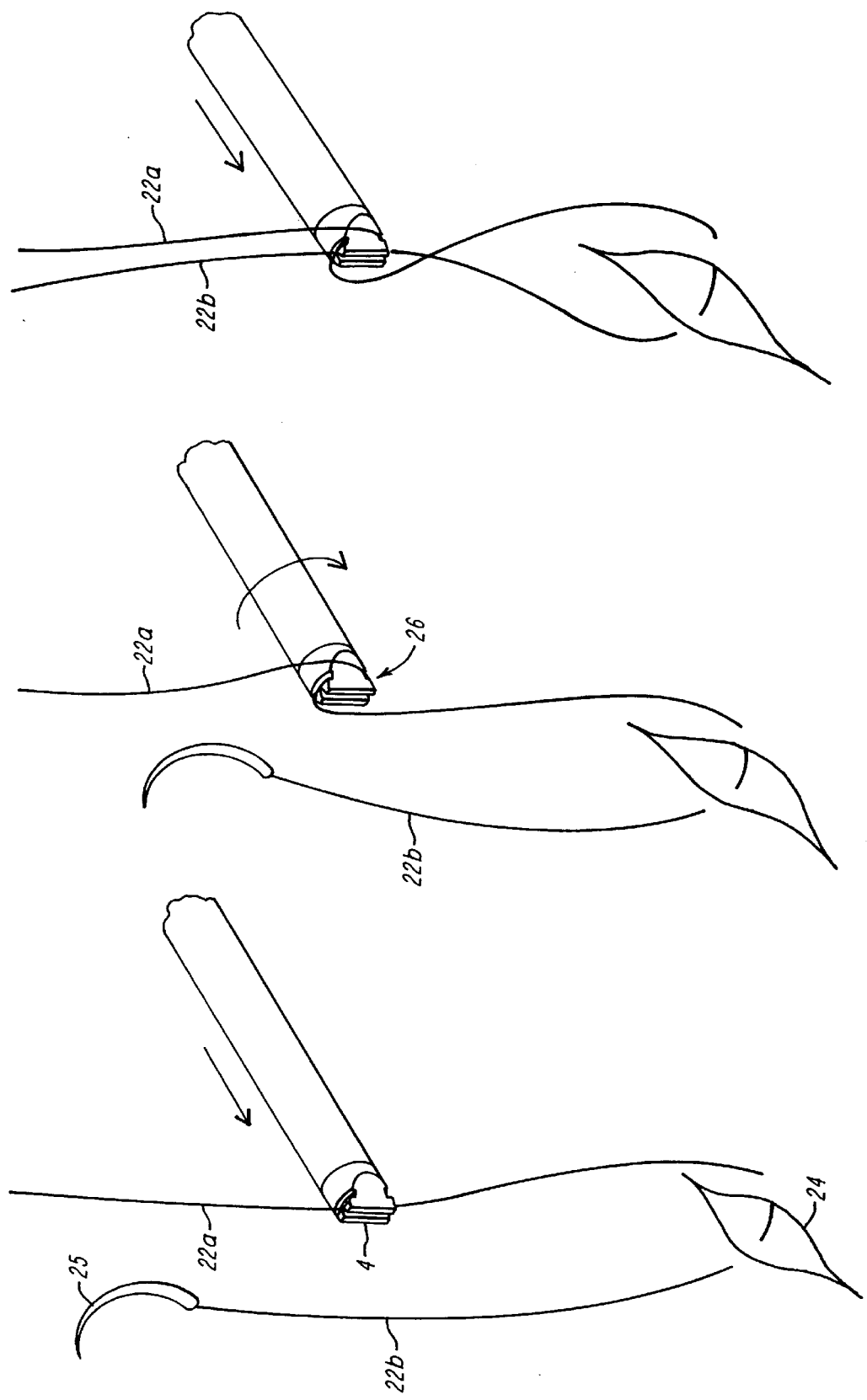

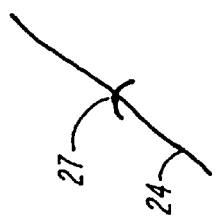
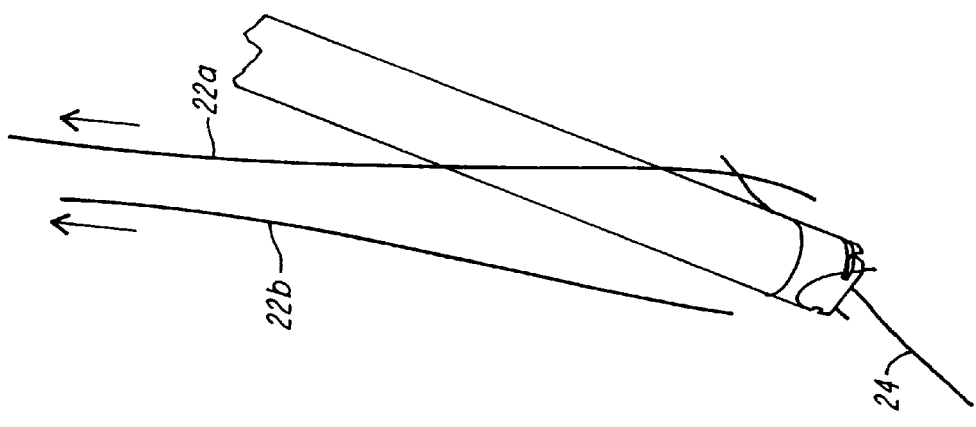
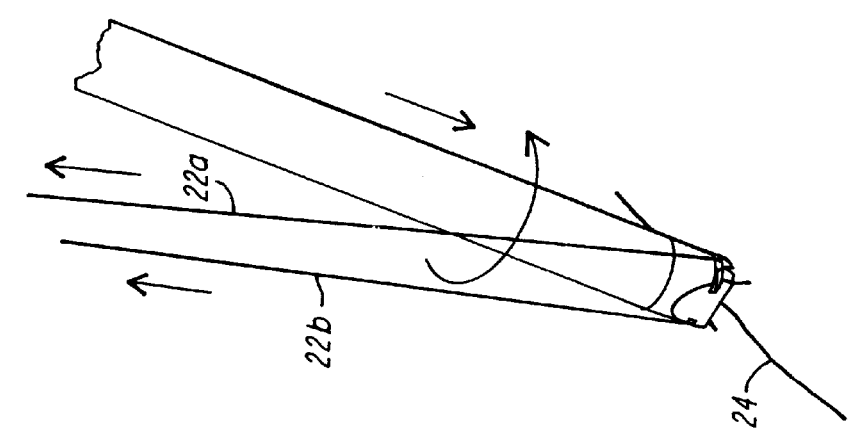
*FIG. 7D*  *FIG. 7E*  *FIG. 7F*

SUTURE FASTENING DEVICE

REFERENCE TO RELATED APPLICATION

This application is a continuation-in-part of U.S. patent application Ser. No. 08/919,297, filed Aug. 28, 1997, now U.S. Pat. No. 5,893,880, granted Apr. 13, 1999. Application Ser. No. 08/919,297 is incorporated by reference herein.

FIELD OF THE INVENTION

The present invention relates generally to closing or joining openings or wounds, tying off vessels, and attaching anatomical and foreign structures in human and animal tissue and the like, and more particularly to devices and methods for suturing, ligating and attaching structures, including hand held devices with specific application and utility in hard to reach surgical situations.

BACKGROUND OF THE INVENTION

U.S. Pat. Nos. 3,513,848 to Winston et al., U.S. Pat. No. 4,662,068 to Polonsky, and U.S. Pat. No. 5,383,883 to Wilk et al. describe joining surgical suture by welding or fusing strands together. The present invention includes significant advances over the prior art.

First among these is control of critical parameters affecting the strength properties of the weld. Principal among these is the force with which the ultrasonic element is brought to bear against the material to be welded. Winston et al. describe a device where this force is provided by the user through pressure applied by the thumb and forefingers. This method of pressure control is subject to substantial variation from weld to weld and from user to user. Similarly, Polonsky and Wilk et al. describe scissors handled instruments with pivoting jaws that apply pressure proportional to the hand pressure of the user. Another critical control parameter is the amount of energy imparted to the weld. Too much energy imparted to the weld would result in complete melting of the weld region, resulting in an amorphous mass of greatly reduced strength. Similarly, too little energy would result in a reduced or absent weld area, also resulting in reduced weld strength. Here again Winston et al., Polonsky and Wilk et al. provide only for timed energy input at the discretion of the user and therefore subject to substantial variation.

Another advance of the present invention over the prior art is the inclusion of means for controlling the morphology of the material in the weld region to produce welds of significantly greater strength than those produced by the apparatus and method described by Winston et al., Polonsky and Wilk et al. Our experience has shown that welds of superior strength are created when the following conditions are satisfied: 1) The weld is configured as a lap weld with load applied from opposite ends of the long axis of the weld (i.e., loaded in shear, not in peel) 2) the area of the welded region is large, 3) a substantial portion of the suture on either side of the weld area has not been subjected to sufficient heat to reduce the tensile strength of the material, and 4) there is a gradual transition from the stressed full cross section of material outside the weld region to the point where the maximum proportion of cross section has been sacrificed to melting to form the weld. Polonsky and Wilk et al. describe the exiting ends of the suture being welded in an orientation such that loads placed upon the suture would subject the weld to peeling stress. Winston et al. describe welds that would load in peel and others in shear, however those loaded in shear are formed by crossing the suture, a practice resulting in weld areas limited to the small region where the segments overlap in a crosswise fashion. Similarly, Polonsky and Wilk et al. refer to twisting the suture, yielding the same end result as crossing the strands. In order to preserve a non-melted (and therefore non-weakened) portion of the material cross section outside of the weld area, melting must be localized to the region where the overlapping segments of suture abut each other. This condition is best accomplished in ultrasonic welding a lap joint when the two segments to be joined are acoustically coupled to structures that vibrate relative to each other. Experience has shown that acoustic coupling is best accomplished by large areas of contact with the vibrating and non-vibrating or counter-vibrating structures. Winston et al describe "welding tips having a small area of contact" and Winston et al., Polonsky and Wilk et al. show flat welding surfaces in contact with round suture, a situation resulting in thin, line contact of a small area. The present invention includes surfaces which conform to the suture to maximize acoustic coupling. A further advance over Winston et al., Polonsky and Wilk et al. is the inclusion of means to facilitate loading suture into the device in an orientation conducive to optimum weld characteristics in vivo. Winston et al., Polonsky and Wilk et al. require the user to cross or twist the suture and place it into a slot in the device. This maneuver is difficult to perform in laparoscopic surgery and would likely require withdrawing the suture ends and the instrument from the body cavity for suture loading. In the present invention, suture ends need only be held under slight tension and a simple grab-twist-grab motion employed to load the suture. Another advantage of the present invention over Winston et al is its means for releasing the finished stitch from the device without compressing tissue inside the stitch or stretching the suture material. The present invention also represents an advance over Winston et al. by including a welding apparatus structure constructed with an elongated shaft suitable for use in minimally invasive surgery (MIS) where suturing must be performed internally through a small incision, or where the instrument must be introduced through a tubular structure. Further advances over Winston et al. and Wilk et al. include a means for cutting the exiting ends of the suture.

It is an object of the present invention to provide an instrument for joining lengths of polymer suture material in areas of difficult or limited access, such as in minimally invasive surgery (MIS).

It is a further object of the present invention to provide an instrument with means to provide a stitch for tissue approximation wound closure, ligating, attachment or suture anchoring functions.

It is a further object of the present invention to provide an instrument with means to provide an attached structure with exiting strands to be used for further tissue approximation, wound closure, ligating, attachment or suture anchoring functions.

It is a further object of the present invention to provide an instrument with means to facilitate loading suture material strands in areas of difficult or limited surgical access.

It is a further object of the present invention to provide an instrument with means for releasing joined surgical suture loops without stretching the loop or compressing the tissue material within the loop.

It is a further object of the present invention to provide an instrument with means for facilitating sliding passage of at least one of the suture material strands exiting a loop to facilitate tensioning of the loop.

It is a further object of the present invention to provide an instrument with means for clamping or securing one suture material strand exiting a loop to facilitate tensioning of the loop by pulling on the remaining, non-secured strand.

It is a further object of the present invention to provide an instrument with means for cutting one or more of the strands of suture material exiting the tensioned, joined, finished loop.

It is a further object of the present invention to provide an instrument with means for shielding the tissue to be sutured from direct contact with the vibrating ultrasonic member, thereby protecting the tissue from injury.

It is a further object of the present invention to provide an instrument with means for removing and replacing tissue contacting portions of the device to assist in maintaining sterility through disassembly for cleaning, or disposal and replacement of the tissue contaminated elements.

It is a further object of the present invention to provide an instrument with means for controlling the force with which the segments of material to be welded are held together before, during and after the welding process.

It is a further object of the present invention to provide an instrument with means for controlling the total weld energy imparted to the segments to be welded.

SUMMARY OF THE INVENTION

According to one aspect of the invention, there is provided a device for forming a welded joint in an elongated material used to ligate living tissue. The device comprises:
  a handle portion;
  an elongated tubular shaft portion extending from the handle portion to a distal end;
  a welding structure at the distal end of the shaft and including an element adapted for accepting two or more segments of the elongated material therein and orienting the segments so that they are overlapped in a joint region with a preselected directionality, the welding structure further including a contoured horn movable axially within the shaft, and a contoured anvil movable axially within the shaft and relative to the horn, the anvil at least partially surrounding the horn;
  an element adapted for actuating the horn and anvil for relative movement to effect a welded joint in the segments of elongated material; and
  a power supply for providing a source of energy to the welding structure.

In a preferred embodiment of the device, the anvil is a split structure adapted for transverse movement relative to the horn so as to effect closure of the anvil about a portion of the horn. The anvil can be split either symmetrically or asymmetrically.

In a preferred embodiment, the segments are overlapped so that they share a common directionality in the joint region.

At least one of the horn and the anvil is contoured for maximum contact with the elongated material.

The device can further comprise a severing element on at least one of the horn and the anvil, which is adapted to cause localized melting of a suture segment in proximity thereto.

In a preferred embodiment, the element for actuating the horn and anvil for movement relative to one another includes a trigger on the handle and connected to the horn and anvil, a first spring disposed within the handle and coupled with the horn for biasing the horn toward the distal end of the shaft, and a second spring disposed within the tubular shaft for biasing the anvil away from the distal end of the shaft.

The device can further include an element detecting a characteristic of at least one of the welding structure and the welded joint after actuation of the horn and anvil, and an element for controlling the delivery of energy to the welding structure when the characteristic reaches a predetermined value. In a preferred embodiment, this latter element comprises a switch for making or breaking an electrical circuit when the characteristic reaches a predetermined value. In one embodiment, the characteristic to be detected is displacement of the horn relative to the anvil after actuation of the horn and anvil. In this embodiment, the detecting element comprises a linear displacement gauge which may be located on the horn or the anvil or on a structure which is stationary relative to the horn.

In an alternate embodiment, the characteristic to be detected is time elapsed after actuation of the horn and anvil. In this embodiment, the detecting element comprises a clock.

In still another embodiment, the characteristic to be detected is force exerted by the horn on the segments after actuation of the horn and anvil and during welding of the segments. In this embodiment, the detecting element comprises a transducer. The power supply preferably comprises an ultrasonic signal generator and an ultrasonic transducer coupled to the horn of the welding structure.

These and other features of the invention will be more fully appreciated with reference to the following detailed description which is to be read in conjunction with the attached drawings.

BRIEF DESCRIPTION OF THE DRAWINGS

FIG. 1a is an isometric view of the device, according to a preferred embodiment, FIG. 1b is a detail isometric view of the tip of the device, FIG. 7a through 7f are views of sequential steps used in one type of suturing performed according to the present invention.

DETAILED DESCRIPTION OF THE DRAWINGS

Figure 2A:
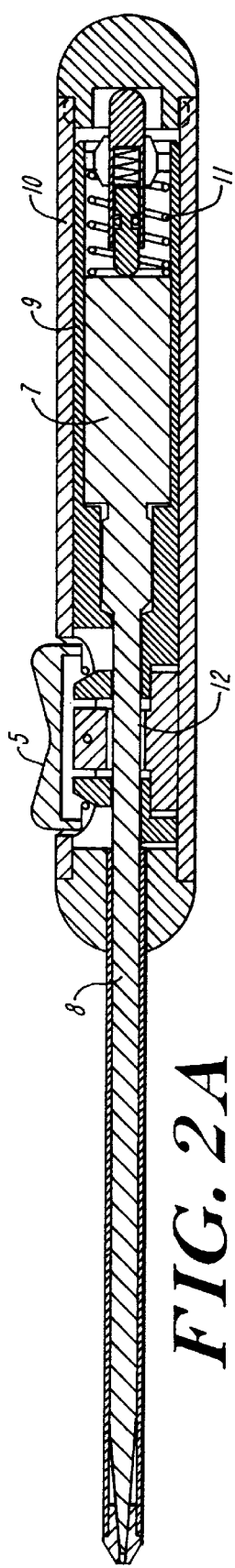
FIG. 2a is section view of the device; anvils closed, horn retracted.

FIG. 1a shows a preferred embodiment of the present invention is expressed as a suture joining device 1 comprising a handle portion 2, a shaft portion 3 of a length and diameter appropriate for introduction through a laparoscopic trocar cannula, and a slotted tip portion 4 at the distal end of the shaft. In a preferred embodiment a three position mechanical actuator 5 is included to control the suture capture, weld and release functions of the device. Other embodiments employ motors, solenoids, pneumatics and other actuating technology known to the art to control the mechanical elements. One preferred embodiment includes an ultrasonic signal generator 6 connected to the handle portion 2 by an electrical cable. Other preferred embodiments provide a self-contained ultrasonic signal generator and battery or other power source in the handle portion 2 itself.

Figure 2B:
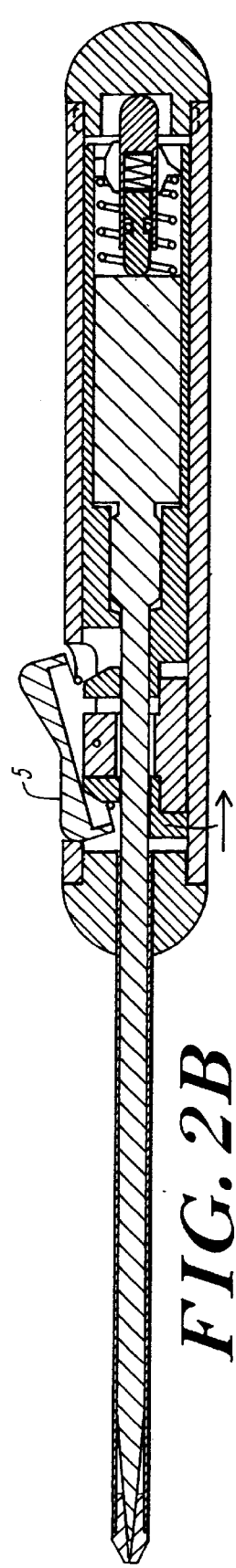
FIG. 2b is section view of the device; anvils open, horn retracted.
Figure 2C:
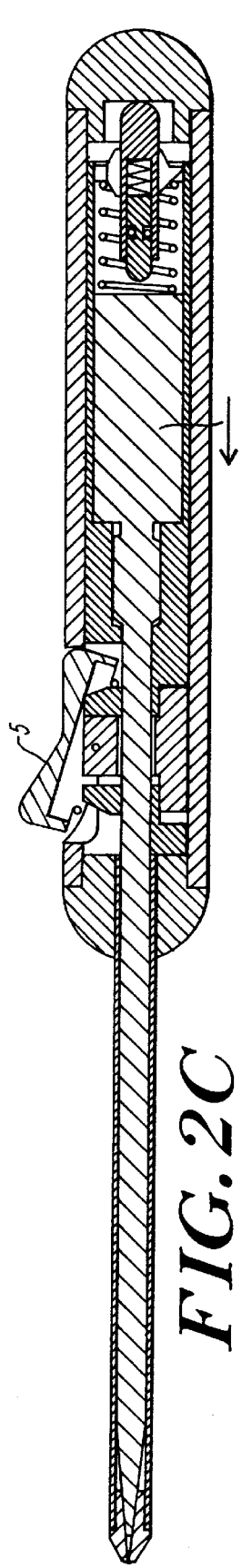
FIG. 2c is section view of the device; anvils closed, horn engaged.

Referring to FIG. 2a, the handle houses an ultrasonic transducer 7 coupled to a tuned ultrasonic horn 8. The transducer and horn are free to slide axially inside a housing 9 which in turn is free to slide axially inside the handle shell 10. Spring 11 biases the transducer 7 and horn 8 in a distal direction within the housing 9. The force applied by spring 11 is equal to the optimum horn force required to achieve peak weld properties when compressed to the weld position. Spring 12 biases the housing 9 and its contents in a proximal direction. Actuator 5 is constructed to perform the dual function of opening the slotted tip 4 allowing the instrument to receive suture strands (actuator 5 position shown in FIG. 2b) and to initiate the welding process (actuator 5 position shown in FIG. 2c).

Figure 3:
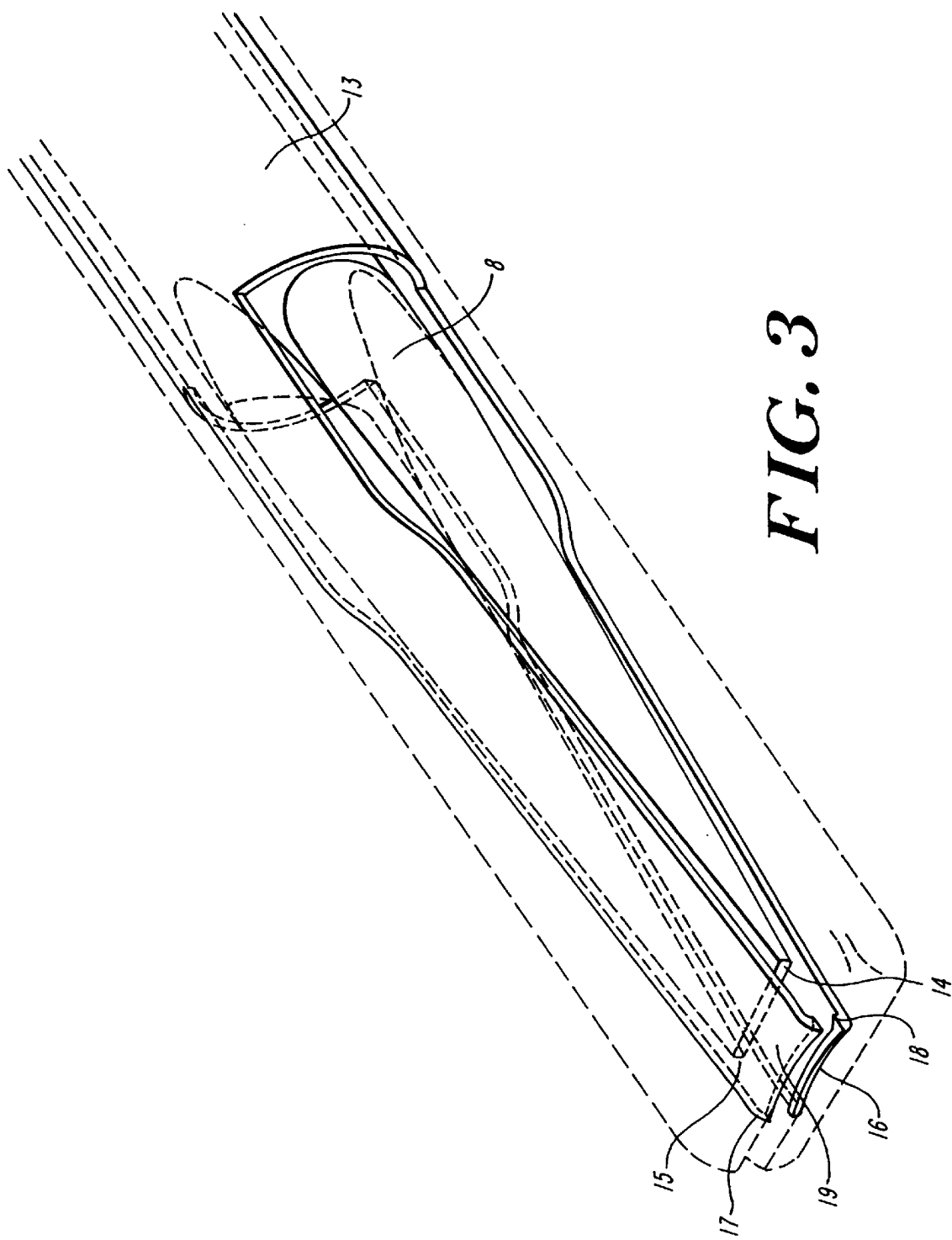
FIG. 3 is a detail isometric view of the tip with exterior components removed.

FIG. 3 shows the interior of the distal end of the device with the tubular shaft 3 and the slotted tip 4 removed. Here we see the distal end of the horn 8 and a tubular inner shaft 13. The horn 8 terminates in a radiused conforming surface 14 designed to conform to the shape of the suture to maximize contact area where limited by the width of the horn 8 and half the circumference of the suture. Other embodiments employ V-shaped, faceted or non-circular contours to increase contact area beyond that attainable by a flat surface. In one embodiment, a protruding edge 15 is present at one end of the radiused conforming surface 14. The tubular inner shaft 13 terminates in an anvil structure 16 which, in the illustrated embodiment, is a substantially open, or split, structure which is adapted for transverse movement to close about a portion of the horn. When the two halves of the split anvil structure 16 are brought together they form a radiused conforming surface 17 similar to the radiused conforming surface 14 on the horn, and like the horn can employ a number of geometries to maximize contact surface area. Also, like horn conforming surface 14, anvil conforming surface 17 is provided with a protruding edge 18. In other embodiments, where severing the loose ends of the suture is not required or where the ends are trimmed manually, protruding edges 15 and 18 are absent. In the preferred embodiment, there exists a relative curvature of the radiused conforming surfaces 14 and 17 in the plane of the axis of the radius of conforming surfaces 14 and 17. On one preferred embodiment (shown) split anvil conforming surface 17 is convex relative to the space between the horn and the anvil 16, while the horn conforming surface 14 is straight. In other embodiments the anvil surface is straight and the horn convex, in still others both are convex but to a lesser degree, others still show the horn concave and the anvil convex but to a greater degree than the concavity of the horn, yet another embodiment is a reverse of the latter. These preceding embodiments can be generalized as having the space 19 between conforming surfaces 14 and 17 exhibit a relative curvature that is convex as viewed from inside the space 19.

Figure 4A:
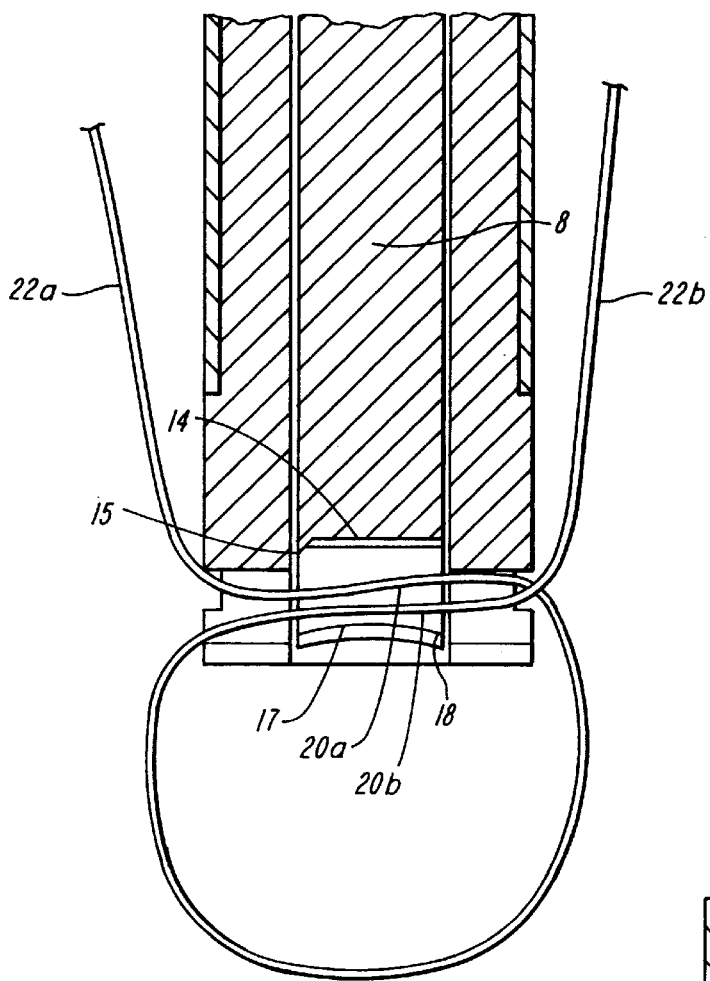
FIG. 4a is a section view of the tip of the device in the x-z plane; anvils open, horn retracted.
Figure 4B:
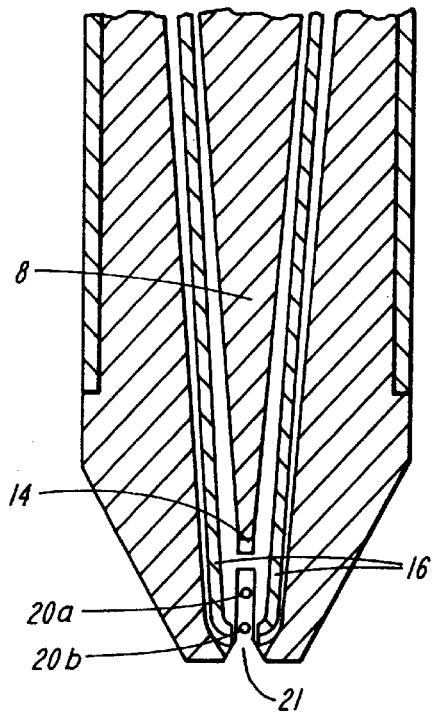
FIG. 4b is a section view of the tip of the device in the y-z plane; anvils open, horn retracted.
Figure 5A:
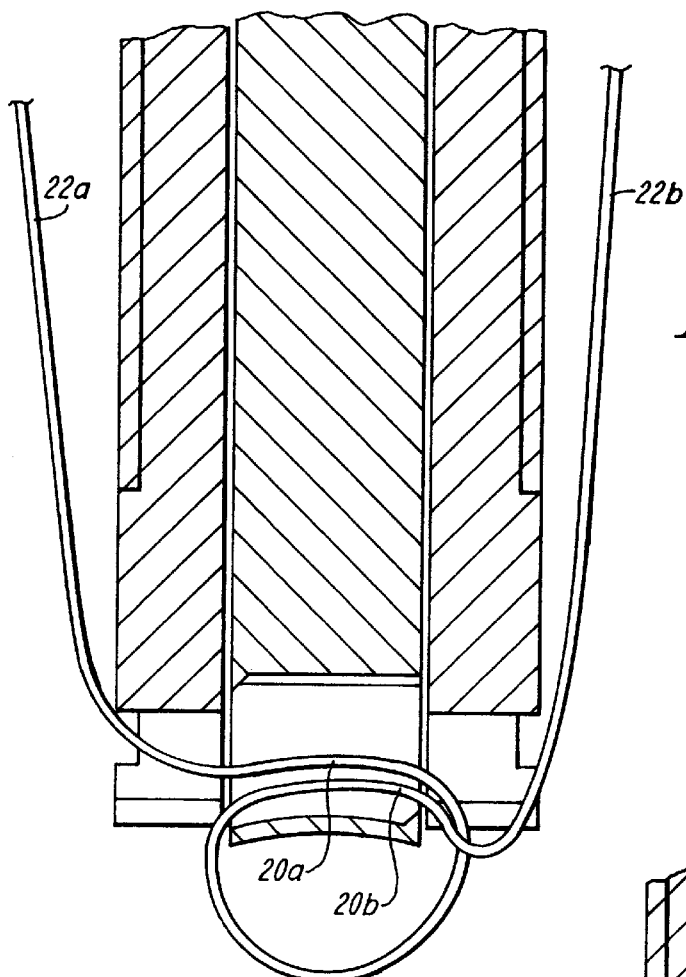
FIG. 5a is a section view of the tip of the device in the x-z plane; anvils closed, horn retracted.
Figure 5B:
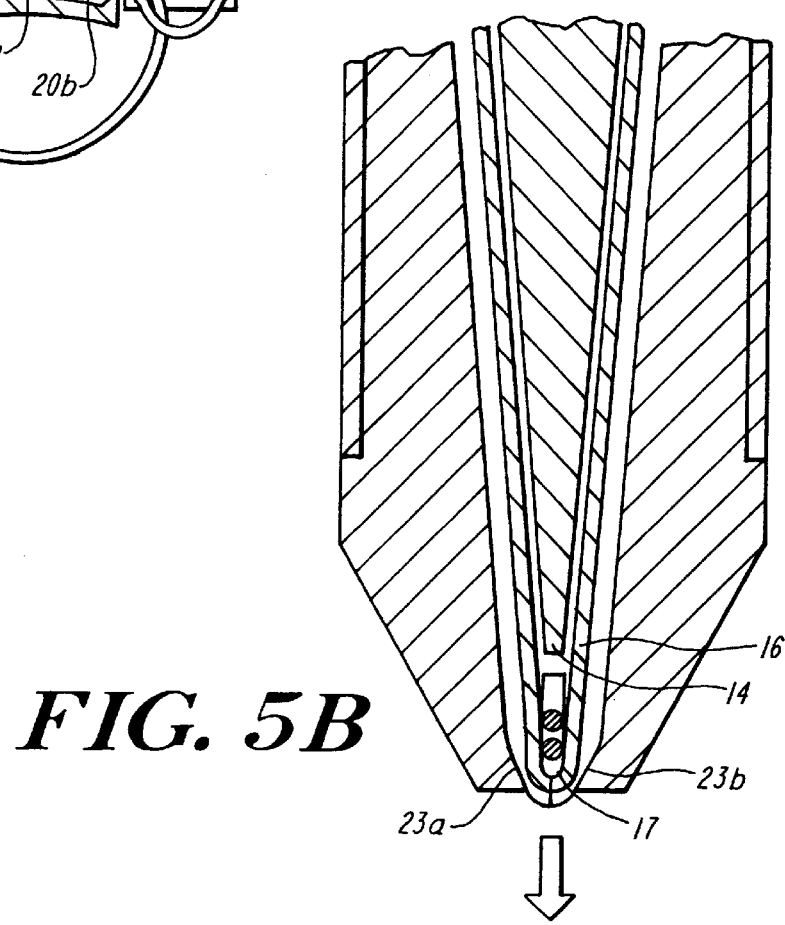
FIG. 5b is a section view of the tip of the device in the y-z plane; anvils closed, horn retracted.

The cooperation of the horn 8 and split anvil 16 in the process of forming a welded suture can be seen in FIGS. 4, 5 and 6. FIG. 4a is a cross section of slotted tip 4 in the plane of the axis of the radius of conforming surfaces 14 and 17 shown with the split anvil structure 16 separated to accept overlapping suture strands 20a and 20b. FIG. 4b is a section view of slotted tip 4 perpendicular to the plane of the axis of the radius of conforming surfaces 14 and 17. In a preferred embodiment, slot 21 in slotted tip 4 has a width equal to or greater than the diameter of the overlapping suture strands 20a and 20b, but less than 2 diameters. In this way overlapping suture strands 20a and 20b can enter the slot only if parallel and not crossed. In other preferred embodiments slot 21 is slightly narrower than the diameter of suture strands 20a and 20b in order to create drag on the exiting strands 22a and 22b during tensioning and to hold them in place during welding. FIGS. 5a and 5b show split anvil 16 approximated, thereby completing formation of anvil conforming surface 17. Approximation of split anvil 16 is performed by displacing tubular inner shaft 13 which terminates in split anvil structure 16 distally relative to split tip 4, and in so doing, the opposed segments of split anvil structure 16, which are biased to spring apart, glide on ramp surfaces 23a and 23b to move toward each other. In one preferred embodiment, opening and closing of the split anvil structure 16 is controlled by operation of actuator 5. Other embodiments employ other actuating means known to the art to accomplish this action. Once split anvil structure 16 is approximated, overlapping suture strands 20a and 20b are captive in slot 21 and can be tensioned by pulling on exiting strands 22a and/or 22b. FIGS. 6a and 6b show overlapping suture strands 20a and 20b being welded together. Horn 8 is displaced distally relative to anvil structure 16. In a preferred embodiment, actuator 5 is exercised to displace housing 9 until horn conforming surface 14 contacts overlapping suture strands 20a and 20b arresting the motion of horn 8 and transducer 7 causing transducer 7 to compress spring 11 thereby compressing overlapping suture strands 20a and 20b against each other and against conforming surfaces 14 and 17 with a predetermined force supplied by spring 11. Ultrasonic transducer 7 is activated causing horn conforming surface 14 to vibrate. Suture strand 20a, being acoustically coupled with large contact area of horn conforming surface 14, vibrates in sympathy with horn 8. Suture strand 20b, being acoustically coupled with large contact area of anvil conforming surface 17, is non-vibrating. Suture strands 20a and 20b, being coupled respectively to vibrating and non-vibrating structures, vibrate against each other and, being substantially round in cross section, concentrate ultrasonic energy along the thin line or point where they contact each other. This concentration of energy where suture strands 20a and 20b make contact results in a buildup of heat, ultimately resulting in localized melting of the suture. Experience has shown that superior weld strength is achieved when a portion of the suture cross section on either side of the weld is not sacrificed to melting and thereby allowed to retain its original, highly linearized molecular orientation. Further, the amount of oriented material on either side of the weld must be controlled precisely to achieve optimum weld strength. A preferred way to control the amount of cross section sacrificed to welding is to control the amount of ultrasonic energy input to the overlapping suture strands 20a and 20b. The preferred embodiment includes means for measuring a characteristic of either the welded joint or the welding structure itself so as to control the energy delivered to the welding structure. Such characteristics include, for example, distance of travel of the horn, time elapsed after actuation of the horn and anvil, and force exerted on the segments by the horn. In one preferred embodiment, the change in displacement of the horn 8 relative to the split anvil structure 16 during the welding process is measured. Ultrasonic energy from the power supply is switched off when the displacement, which is proportional to the volume of material melted, which in turn is proportional to the energy input to the overlapping suture strands 20a and 20b, reaches a predetermined value. In the preferred embodiment the horn 8 maintains a predetermined compressive force on the overlapping suture strands 20a and 20b during the cooling and re-solidification process. This force can be measured and used to control the delivery of energy to the welding horn. Another preferred embodiment provides an electrical contact that is made or broken at a predetermined displacement of the horn 8 relative to the split anvil structure 16 during the welding process and in so doing switches off the ultrasonic energy at the appropriate energy input. In another embodiment, the time elapsed after actuation of the horn and anvil is measured by a clock, and delivery of energy to the welding horn is controlled by interrupting electrical power from the power supply after a predetermined time has elapsed. Other embodiments include controlling energy input directly through electronic measurement and control of power and time. However, this method does not account for ultrasonic energy lost to environmental conditions (particularly the presence of blood and other materials in the weld area) and other variables. Another embodiment provides a physical stop to limit the travel of the horn 8 to a predetermined distance. This embodiment has the disadvantage of disengaging the compressive force applied to the overlapping suture strands 20a and 20b during the cooling and re-solidification process, and thereby affecting the morphology of the weld region of the finished weld.

Other anvil structures are considered to be within the scope of the present invention. Although the anvil structure 16 is illustrated as being substantially symmetrically split, it may also be asymmetrically split, or be otherwise constructed to partially or fully surround the segments to be welded and at least a portion of the horn structure.

Figure 6A:
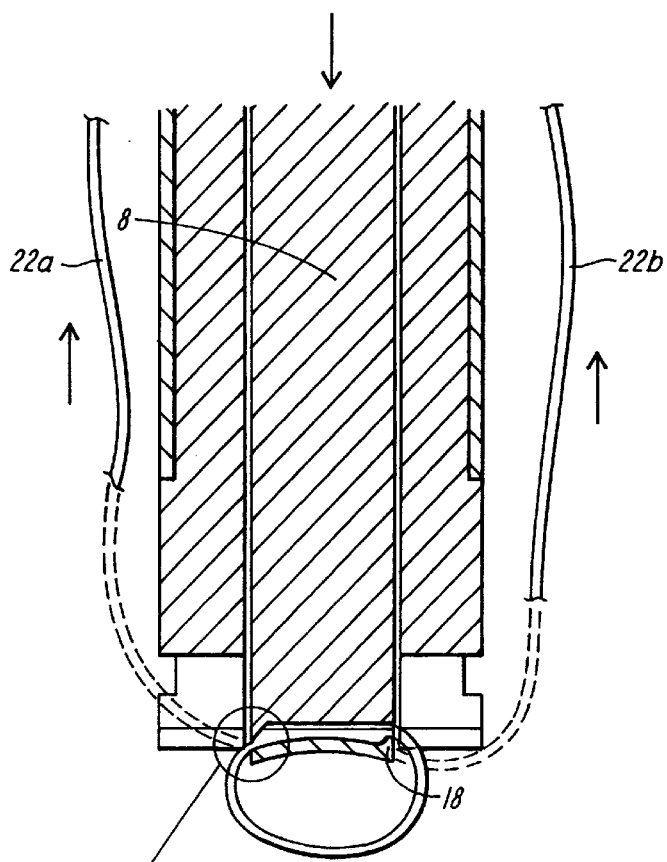
FIG. 6a is a section view of the tip of the device in the x-z plane; anvils closed, horn engaged.
Figure 6B:
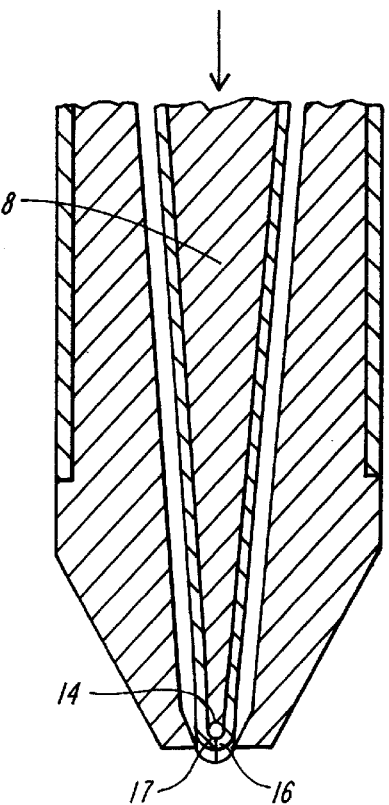
FIG. 6b is a section view of the tip of the device in the y-z plane; anvils closed, horn engaged.
Figure 6C:
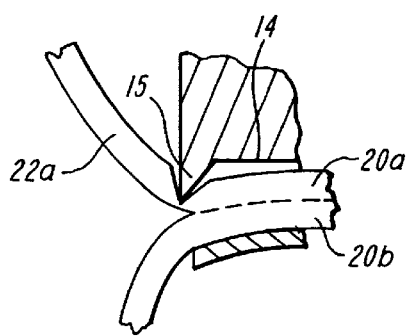
FIG. 6c is a detail section view showing the trim mechanism.
Figure 6D:
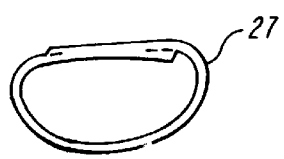
FIG. 6d is a view of the completed, released stitch.

In a preferred embodiment means for severing the exiting strands 22a and 22b are provided, as seen in FIG. 6a and 6c. In one preferred embodiment protruding edges 15 and 18 are present on conforming surfaces 14 and 17. During welding, protruding edges 15 and 18 defeat acoustic coupling of conforming surfaces 14 and 17 at specific locations on the overlapping suture strands 20a and 20b corresponding to the point where exiting strands 22a and 22b connect to overlapping suture strands 20a and 20b at the edges of the weld region. By defeating acoustic coupling at protruding edge 15, overlapping suture strands 20a and 20b preferentially couple with split anvil structure 16, resulting in energy concentration at the interface of protruding edge 15 and suture strand 20a. The result is localized melting at this interface. In a preferred embodiment, the length of protruding edge 15 is sufficient to cause melting through most of the cross section of strand 20a, such that it is still attached to the exiting strand 22a but able to be separated from strand 20a by a gentle tug on exiting strand 22a. The preceding scenario is duplicated where overlapping suture strands 20a and 20b preferentially couple with horn 8 in the vicinity of protruding edge 18, resulting in near complete severing of the interface of overlapping strand 20b and exiting strand 22b. In other preferred embodiments the strands are severed completely. In still other embodiments the strands are left fully intact for manual trimming or to allow the exiting strands to be used for further tissue approximation, wound closure, ligating or suture anchoring functions.

In the preferred embodiment the device is operated as shown in FIGS. 7a through 7f. FIG. 7a shows a wound 24 to be closed by suture. A suture needle 25 is passed through either side of the wound leaving exiting strands 22a and 22b. With split anvil structure 16 in the open position, strand 22a is slid into slot 21 in slotted tip 4. FIG. 7b shows the device 1 rotated 180 degrees. Strand 22a is prevented slipping free from tip 4 by circumferential retaining slot 26. FIG. 7c shows strand 22b slid into slot 21. At this point split anvil structure 16 can be approximated by exercising actuator 5 on handle portion 2, thereby capturing strands 22a and 22b and positioning overlapping suture strands 20a and 20b. FIG. 7d shows exiting strands 22a and 22b held under tension while slotted tip 4 is slid into close proximity with wound 24 holding the edges of the wound 24 closed. FIG. 7e shows the welding/cutting step where overlapping suture strands 20a and 20b are joined and exiting strands 22a and 22b are trimmed free. FIG. 7f shows the completed stitch 27 released from the instrument by opening split anvil structure 16. In other embodiments of the device and method of surgery suture is used to surround a vessel (e.g. ligation, etc.), attach or suspend an anatomical or foreign structure (e.g. bladder neck suspension, mesh or film attachment, grafting, anastomosis, etc.) or create other stitch forms (e. g. subcutaneous, mattress, anchor for running stitch, etc.).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

We claim:

1. A device for forming a welded joint in an elongated surgical suture material, said device comprising:

a handle portion;

an elongated tubular shaft portion extending along an axis from said handle portion to a distal end;

a welding structure at the distal end of said shaft, said welding structure including a channel open to the distal end and extending transverse to the axis for accepting two or more segments of said elongated material therein, said segments being overlapped in the channel in the direction of the axis in a joint region, said welding structure further including a contoured horn movable axially within said shaft, and a contoured anvil movable axially within said shaft and relative to said horn, said anvil at least partially surrounding said horn;

means for actuating said horn and anvil for relative movement to effect a welded joint in said segments of said elongated material; and means for providing energy to the welding structure.

2. A device according to claim 1, wherein the anvil is a split structure adapted for transverse movement relative to said horn so as to effect closure of the anvil about a portion of the horn.

3. A device according to claim 1, wherein the segments are overlapped so that they share a common directionality in the joint region.

4. A device according to claim 1, wherein at least one of the horn and the anvil is contoured for maximum contact with the elongated material.

5. A device according to claim 1, further comprising a severing element on at least one of the horn and the anvil, whereby the severing element is adapted to cause localized melting of a suture segment in proximity thereto.

6. A device according to claim 1, wherein the means for actuating the horn and anvil for movement relative to one another includes trigger means on the handle and connected to the horn and anvil, first spring means disposed within the handle and coupled with the horn for biasing the horn toward the distal end of the shaft, and second spring means disposed within the tubular shaft for biasing the anvil away from the distal end of the shaft.

7. A device according to claim 6, further comprising means for detecting a characteristic of at least one of the welding structure and the welded joint after actuation of the horn and anvil, and means for controlling the delivery of energy to the welding structure when the characteristic reaches a predetermined value.

8. A device according to claim 7, wherein the means for controlling the delivery of energy to the welding structure comprises a switch for making or breaking an electrical circuit when the characteristic reaches a predetermined value.

9. A device according to claim 7, wherein the characteristic is displacement of the horn relative to the anvil after actuation of the horn and anvil.

10. A device according to claim 7, wherein the characteristic is time elapsed after actuation of the horn and anvil.

11. A device according to claim 7, wherein the characteristic is force exerted by the horn on the segments after actuation of the horn and anvil and during welding of the segments.

12. A device according to claim 1, wherein the means for providing a source of energy comprises an ultrasonic signal generator and an ultrasonic transducer coupled to the horn of the welding structure.

13. A device for forming a welded joint in a fusible surgical suture material, said device comprising:

- an elongated tubular shaft extending along an axis from a proximal end to a distal end;
- a welding horn extending from the proximal end of said tubular shaft through the shaft to a distal end and being selectively movable in the direction of the axis;
- a welding anvil extending from the shaft to a distal end and partially surrounding the welding horn, the welding anvil and welding horn defining a channel selectively open to the distal end extending transverse to said axis and adapted to receive two or more overlapping segments of a fusible surgical suture material, one segment contacting the welding horn and the remaining segments contacting one another and portions of the welding anvil, the segments being overlapped in the direction of the axis; and
- an energy source associated with the device for transmitting energy through the welding horn to the overlapping segments, thereby effecting localized heating and plastic flow of the overlapping segments.

14. A device according to claim 13, wherein the distal end of at least the welding horn includes an arcuate contour for defining the contact area between the welding horn and a segment in contact therewith.

15. A device according to claim 13, wherein the device further includes an exterior housing disposed about the shaft and the welding anvil.

16. A device according to claim 15, wherein the welding anvil includes two cantilevered fingers having distal ends which define a base of the open channel, and wherein the housing is adapted for sliding motion relative to the welding anvil, wherein the fingers are resiliently biased apart, and wherein axially directed sliding motion of the housing over the fingers toward their distal ends compresses the fingers together to form a closed channel.

* * * * *